US011020331B2

(12) United States Patent
Koizumi et al.

(10) Patent No.: US 11,020,331 B2
(45) Date of Patent: Jun. 1, 2021

(54) COSMETIC

(71) Applicant: SAKAI CHEMICAL INDUSTRY CO., LTD., Sakai (JP)

(72) Inventors: Hisao Koizumi, Osaka (JP); Momoko Ishikawa, Osaka (JP); Nanae Ogata, Osaka (JP); Kenji Mori, Osaka (JP)

(73) Assignee: Sakai Chemical Industry Co., Ltd., Osaka (JP)

( * ) Notice: Subject to any disclaimer, the term of this patent is extended or adjusted under 35 U.S.C. 154(b) by 0 days.

(21) Appl. No.: 16/767,946

(22) PCT Filed: Sep. 21, 2018

(86) PCT No.: PCT/JP2018/035054
§ 371 (c)(1),
(2) Date: May 28, 2020

(87) PCT Pub. No.: WO2019/106920
PCT Pub. Date: Jun. 6, 2019

(65) Prior Publication Data

US 2020/0297598 A1 Sep. 24, 2020

(30) Foreign Application Priority Data

Nov. 29, 2017 (JP) ............................. JP2017-228997
Mar. 22, 2018 (JP) ............................. JP2018-055011
Jun. 1, 2018 (JP) ............................. JP2018-106090

(51) Int. Cl.
*A61K 8/19* (2006.01)
*A61Q 1/12* (2006.01)
(Continued)

(52) U.S. Cl.
CPC .................. *A61K 8/29* (2013.01); *A61K 8/26* (2013.01); *A61K 8/27* (2013.01); *A61Q 1/10* (2013.01);
(Continued)

(58) Field of Classification Search
CPC ... A61K 8/02; A61K 8/19; A61K 8/24; A61K 8/26; A61K 8/27; A61K 8/29; A61Q 1/10;
(Continued)

(56) References Cited

U.S. PATENT DOCUMENTS 2,585,461 A * 2/1952 Hirsch .................. C09K 11/00 423/622
6,517,628 B1 2/2003 Pfaff et al.
(Continued)

FOREIGN PATENT DOCUMENTS

JP 3-284613 12/1991
JP 2000-044828 2/2000
(Continued)

OTHER PUBLICATIONS

Abstract of JP05117127 1993; 1 page. (Year: 1993).*
(Continued)

*Primary Examiner* — Ernst V Arnold
(74) *Attorney, Agent, or Firm* — Hamre, Schumann, Mueller & Larson, P.C.

(57) ABSTRACT

The present invention provides a cosmetic product capable of making the skin look youthful and producing a natural three-dimensional appearance. The present invention relates to a cosmetic product including two or more phosphors each containing an inorganic compound, wherein the cosmetic product, upon excitation by excitation light having a wavelength of 365 nm, emits an emission spectrum having a fluorescence emission peak in each of the range of 400 to 530 nm and the range of 620 to 720 nm and having an $I_2/I_1$ of 1 to 30, where $I_1$ is a maximum emission intensity in the range of 530 to 620 nm and $I_2$ is a maximum peak intensity in the range of 620 to 720 nm.

7 Claims, 4 Drawing Sheets

(51) Int. Cl.

| | |
|---|---|
| ***C09K 11/54*** | (2006.01) |
| ***A61K 8/27*** | (2006.01) |
| ***A61K 8/24*** | (2006.01) |
| ***A61K 8/29*** | (2006.01) |
| ***A61K 8/26*** | (2006.01) |
| ***A61Q 1/10*** | (2006.01) |
| ***C09K 11/57*** | (2006.01) |
| ***C09K 11/64*** | (2006.01) |

(52) U.S. Cl.
CPC ................ *A61Q 1/12* (2013.01); *C09K 11/54* (2013.01); *C09K 11/57* (2013.01); *C09K 11/643* (2013.01)

(58) Field of Classification Search
CPC .......... A61Q 1/12; C09K 11/54; C09K 11/57; C09K 11/643
See application file for complete search history.

(56) References Cited

U.S. PATENT DOCUMENTS

| | | | | |
|---|---|---|---|---|
| 9,937,114 | B2 * | 4/2018 | Sako | A61Q 1/02 |
| 2002/0012681 | A1 | 1/2002 | George et al. | |
| 2017/0027827 | A1 * | 2/2017 | Ota | A61Q 17/04 |
| 2017/0065498 | A1 * | 3/2017 | Gershon | A61K 8/0275 |
| 2017/0202759 | A1 | 7/2017 | Sako et al. | |

FOREIGN PATENT DOCUMENTS

| | | | |
|---|---|---|---|
| JP | 2000-345096 | 12/2000 | |
| JP | 2002-326911 | 11/2002 | |
| JP | 2005-097218 | 4/2005 | |
| JP | 2005-206613 | 4/2005 | |
| JP | 2006-249012 | 9/2006 | |
| JP | 2006-316065 | 11/2006 | |
| JP | 2008-050312 | 3/2008 | |
| JP | 2016-132650 | 7/2016 | |
| JP | 2016-141780 | 8/2016 | |
| WO | WO-2015166895 A1 * | 11/2015 | A61K 8/0245 |
| WO | 2016/017372 | 2/2016 | |

OTHER PUBLICATIONS

Abstract of JP2017122076 2017; 1 page. (Year: 2017).*

Ono, "Development of luminescent powder and its application to cosmetics", Fragrance Journal, Feb. 1994, pp. 11-16—partial translation.

Sakurai, et al., "Current status and issues of recent research and development of foundation", Fragrance Journal, May 2000, pp. 13-18—partial translation.

Mitsui, New Cosmetic Science, 2nd Edition, Nanzando Co., Ltd., Jan. 18, 2001, pp. 78-110—see the Written Opinion, cited herein, for a concise explanation of relevance.

Written Opinion of the International Searching Authority issued in International Application No. PCT/JP2018/035054, dated Oct. 30, 2018, 16 pages with an English translation.

* cited by examiner

COSMETIC

TECHNICAL FIELD

The present invention relates to cosmetic products, and more particularly to cosmetic products capable of giving a three-dimensional appearance to the skin.

BACKGROUND ART

There are various cosmetic products, including foundations, lipsticks, and eye shadows. Various products are on the market to meet consumer's exact preferences. One of the effects desired for such cosmetic products is to obscure the appearance of skin darkening or blemishes to make the skin look youthful. Another desired effect is to produce a three-dimensional appearance of the face. To produce a three-dimensional appearance by makeup, foundations having different colors may be applied to give contrast, or nose shadow may be applied to make the bridge of the nose look thinner. However, these methods require the use of additional highlighters after the application of usual makeup. The methods also require special makeup techniques (e.g., the way the skin looks differs depending on what kinds of highlighters are used and where and in what order they are applied), and cause color difference noticeable when the face is viewed from the side, giving an unnatural finish. Thus, there is a demand for a cosmetic product that gives a natural three-dimensional appearance without these complications.

To produce such an effect, a pigment mixture has been disclosed, which includes a component containing a predetermined multilayer pigment and a component containing a flake-shaped, needle-shaped, or spherical colorant and/or filler (see Patent Literature 1). A foundation or makeup base has been also disclosed, which contains a pearl pigment of a predetermined particle size and a spherical resin powder at a predetermined ratio. Other various cosmetic products containing phosphors have also been disclosed (see Patent Literatures 2 to 9).

CITATION LIST

Patent Literature

Patent Literature 1: JP 2000-345096 A
Patent Literature 2: JP 2005-97218 A
Patent Literature 3: JP 2006-316065 A
Patent Literature 4: JP 2005-206613 A
Patent Literature 5: JP 2008-50312 A
Patent Literature 6: JP 2000-44828 A
Patent Literature 7: JP 2002-326911 A
Patent Literature 8: JP 2006-249012 A
Patent Literature 9: JP 2016-132650 A

SUMMARY OF INVENTION

Technical Problem

As mentioned earlier, various cosmetic products have been proposed. However, in the case of the cosmetic product of Patent Literature 1, for example, only the area to which the powder is applied glows unnaturally. It does not give a natural three-dimensional appearance as that of a freshly peeled boiled egg, where the high points look glowing from every angle.

To make the face look youthful, not only the natural three-dimensional appearance but also a beautiful, translucent glow of the skin is required. A beautiful skin reflects a lot of red light and blue light because a beautiful skin allows light to penetrate it deeply and the light is absorbed by blood, which has significant light absorption regions at 540 nm and 578 nm. Therefore, one makeup technique that has been used to make the skin look beautiful is to add red or bluish green pigments to cosmetic products, thereby imitating the way a beautiful skin looks. This technique, however, merely colors the skin with pigments, and thus results in an unnatural appearance because the way the skin with such pigments looks is completely different from the way the skin looks with natural light reflection. The cosmetic composition of Patent Literature 3 includes a mixture of multiple inorganic phosphors to give at least three types of emission peaks, thus achieving emission of white light to make the skin look brighter. However, also this cosmetic composition has a reflection spectrum completely different from that of a beautiful skin, and the emission of white light is artificial and very unnatural. Thus, the youthful and natural three-dimensional appearance has not been achieved using a cosmetic product containing a phosphor. Other cosmetic products of Patent Literatures 2 and 4 to 9 also fail to exhibit a sufficient effect in this regard.

In view of the situation in the art, the present invention aims to provide a cosmetic product capable of making the skin look youthful and producing a natural three-dimensional appearance.

Solution to problem

The present inventors studied cosmetic products that can solve the above problems. They found out that the following cosmetic product can make the skin look youthful and produce a natural three-dimensional appearance: a cosmetic product including two or more phosphors each containing an inorganic compound, wherein the cosmetic product, upon excitation by excitation light having a wavelength of 365 nm, emits an emission spectrum having a fluorescence emission peak in each of the range of 400 to 530 nm and the range of 620 to 720 nm and the ratio of a maximum peak intensity in the range of 620 to 720 nm to a maximum emission intensity in the range of 530 to 620 nm is within a specific range. The inventors thus completed the present invention.

The present invention relates to a cosmetic product including two or more phosphors each containing an inorganic compound, wherein the cosmetic product, upon excitation by excitation light having a wavelength of 365 nm, emits an emission spectrum having a fluorescence emission peak in each of the range of 400 to 530 nm and the range of 620 to 720 nm and having an $I_2/I_1$ of 1 to 30, where $I_1$ is a maximum emission intensity in the range of 530 to 620 nm and $I_2$ is a maximum peak intensity in the range of 620 to 720 nm.

In the cosmetic product, the emission spectrum emitted upon excitation by excitation light having a wavelength of 365 nm preferably has an $I_2/I_3$ of 1 to 40, where $I_3$ is a maximum peak intensity in the range of 400 to 530 nm and $I_2$ is the maximum peak intensity in the range of 620 to 720 nm.

The cosmetic product preferably has an emission color with an x value of the CIE chromaticity coordinates in the range of 0.25 to 0.55 and a y value of the CIE chromaticity coordinates in the range of 0.22 to 0.42 upon excitation by excitation light having a wavelength of 365 nm.

The cosmetic product preferably contains a mixture containing:

a phosphor containing at least one selected from the group consisting of a complex oxide containing Mn in a compound of the following formula (1), the Mn being present in a proportion of 0.00005 to 0.05 mol relative to 1 mol of magnesium in the compound:

$$Mg_xTi_yO_z \quad (1)$$

wherein x, y, and z satisfy 1.5<x<2.5, 0.5<y≤1.5, and z=x+2y, and a complex oxide containing Mn in a compound of the following formula (2), the Mn being present in a proportion of 0.000042 to 0.0083 mol relative to 1 mol of aluminum in the compound:

$$Ca_xAl_yO_z \quad (2)$$

wherein x, y and z satisfy 0.1<x<1.05, 11.9<y≤12, and z=(2x+3y)/2; and a phosphor containing at least one selected from the group consisting of a complex oxide containing Ce in a compound of the following formula (3), the Ce being present in a proportion of 0.0005 to 0.05 mol relative to 1 mol of phosphorus in the compound:

$$Ca_xP_yO_x \quad (3)$$

wherein x, y and z satisfy 3.2≤x≤5.0, 1.9≤y≤2.1, and z=x+5, and a fluorescent zinc oxide.

The cosmetic product preferably has a phosphor content of 0.1 to 20% by weight relative to the entire cosmetic product.

The cosmetic product preferably has an internal quantum efficiency of 1 to 40% upon excitation by excitation light having a wavelength of 365 nm.

The cosmetic product is preferably in a form selected from powder foundations, liquid foundations, face powders, eye shadows, and makeup films.

Advantageous Effects of Invention

The cosmetic product of the present invention has emission closer to the glow of a translucent, beautiful skin, and can produce a natural three-dimensional appearance. The cosmetic product thus can make the skin look youthful and enhance the three-dimensional appearance of the face without highlighters or special makeup techniques.

DESCRIPTION OF EMBODIMENTS

Figure 1:
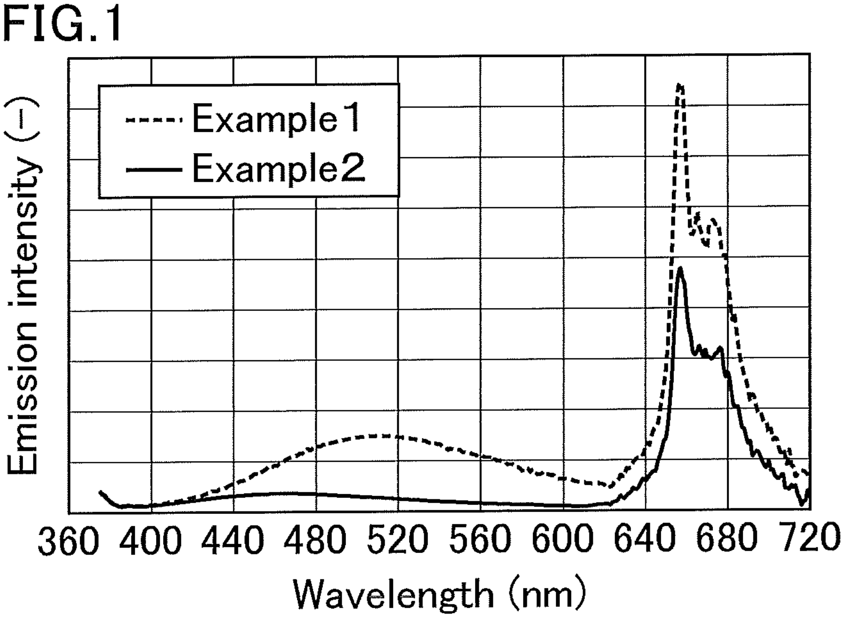
FIG. 1 shows the emission spectrum measurement results of Cosmetic products 1 and 2 obtained in Examples 1 and 2.

Preferred embodiments of the present invention will be described in detail below. The present invention should not be limited to the description below, and appropriate modifications can be made without changing the gist of the present invention.

The cosmetic product of the present invention, upon excitation by excitation light having a wavelength of 365 nm, emits an emission spectrum having a fluorescence emission peak in each of the range of 400 to 530 nm and the range of 620 to 720 nm and having an $I_2/I_1$ of 1 to 30, where $I_1$ is a maximum emission intensity in the range of 530 to 620 nm and $I_2$ is a maximum peak intensity in the range of 620 to 720 nm.

As described earlier, a beautiful skin allows light to deeply penetrate into it. Light penetrating into the skin in the wavelength region of 540 nm to 578 nm is absorbed by blood, while green to blue light in the region of shorter wavelengths than 540 nm and red light in the region of longer wavelength than 578 nm are reflected. The cosmetic product of the present invention has emission similar to the refection spectrum of a beautiful skin (a reflection peak in the blue to green region of 450 to 550 nm and a sharp rise of reflection spectrum from 600 nm toward higher wavelengths). The cosmetic product thus can make the skin look beautiful and youthful.

In the cosmetic product of the present invention, the $I_2/I_1$ is preferably 2 to 29, more preferably 3 to 27, still more preferably 5 to 26.

Here, when a sharp peak at which the emission intensity reaches its maximum is observed in the range of 530 to 620 nm, the term "maximum emission intensity in the range of 530 to 620 nm" means the emission peak intensity at the peak. When no such sharp peak is observed in the range of 530 to 620 nm, the term means the emission intensity at a position at which the emission intensity reaches its maximum in the range of 530 to 620 nm.

In the cosmetic product of the present invention, the emission spectrum emitted upon excitation by excitation light having a wavelength of 365 nm preferably has an $I_2/I_3$ of 1 to 40, where $I_3$ is a maximum peak intensity in the range of 400 to 530 nm and $I_2$ is the maximum peak intensity in the range of 620 to 720 nm.

The light reflection pattern of a beautiful skin has reflected light in both of the wavelength range of 400 to 530 nm and the wavelength range of 620 to 720 nm, with the reflection of light in the wavelength range of 620 to 720 nm being greater than the reflection of light in the wavelength range of 400 to 530 nm. Thus, the cosmetic product of the present invention with an $I_2/I_3$ of 1 to 40 has emission close to the light reflection spectrum of the beautiful skin, further enhancing the effect of making the skin look youthful. The $I_2/I_3$ is more preferably 2 to 30, still more preferably 3 to 25.

$I_1$, $I_2$, and $I_3$ can be measured by the method described in Examples below.

The cosmetic product of the present invention preferably has an emission color with an x value of the CIE chromaticity coordinates in the range of 0.25 to 0.55 and a y value of the CIE chromaticity coordinates in the range of 0.22 to 0.42 upon excitation by excitation light having a wavelength of 365 nm. When the x and y values of the CIE chromaticity coordinates are in the ranges, the cosmetic product of the present invention has an emission color close to white and glows more brightly when illuminated with light, leading to a more natural three-dimensional appearance and sheen. As a results, when the cosmetic product of the present invention is used as a foundation or a makeup base, light gathers on the high points of the face such as the bridge of the nose, the cheekbones, and the middle of the forehead, so that these points look glowing brightly. The cosmetic product thus more sufficiently produces a face having skin elasticity and giving a healthy and youthful impression. The white emission color gives sheen on the area illuminated with light, making it easy to achieve an elastic skin texture like that of a freshly peeled boiled egg. These effects make the cosmetic product of the present invention more suitable as a three-dimensional appearance-imparting cosmetic product.

The x value range is more preferably 0.29 to 0.52, still more preferably 0.32 to 0.45.

The y value range is more preferably 0.26 to 0.41, still more preferably 0.33 to 0.40.

The x and y values can be measured by the method described in Examples below.

In the cosmetic product of the present invention, preferably, the emission spectrum emitted upon excitation by excitation light having a wavelength of 365 nm has a broad fluorescence peak in the range of 400 to 530 nm, and the distance between two points indicating half of the maximum peak intensity in the range of 400 to 530 nm (also referred to as half width or full width at half maximum) is 50 to 200 nm. When the half width is in this range, brightness and blueness can be enhanced, and also natural translucency can be produced.

In the cosmetic product of the present invention, the half width is preferably 100 to 170 nm, more preferably 110 to 160 nm, still more preferably 120 to 150 nm.

The cosmetic product of the present invention contains two or more phosphors each containing an inorganic compound. The cosmetic product may contain any phosphors that have the above predetermined optical characteristics, and preferably contains a mixture containing:

- a phosphor containing at least one selected from the group consisting of
  - a complex oxide containing Mn in a compound of the following formula (1), the Mn being present in a proportion of 0.00005 to 0.05 mol relative to 1 mol of magnesium in the compound:

$$Mg_xTi_yO_z \quad (1)$$

- wherein x, y, and z satisfy $1.5<x<2.5$, $0.5<y\leq1.5$, and $z=x+2y$, and
  - a complex oxide containing Mn in a compound of the following formula (2), the Mn being present in a proportion of 0.000042 to 0.0083 mol relative to 1 mol of aluminum in the compound:

$$Ca_xAl_yO_z \quad (2)$$

- wherein x, y and z satisfy $0.1<x<1.05$, $11.9<y\leq12$, and $z=(2x+3y)/2$; and
- a phosphor containing at least one selected from the group consisting of
  - a complex oxide containing Ce in a compound of the following formula (3), the Ce being present in a proportion of 0.0005 to 0.05 mol relative to 1 mol of phosphorus in the compound:

$$Ca_xP_yO_z \quad (3)$$

- wherein x, y and z satisfy $3.2\leq x\leq5.0$, $1.9\leq y\leq2.1$, and $z=x+5$, and
  - a fluorescent zinc oxide.

In the formula (1), x satisfies $1.5<x<2.5$, preferably $1.7<x<2.3$, more preferably $1.8<x<2.2$, still more preferably $x=2$.

In the formula (1), y satisfies $0.5<y\leq1.5$, preferably $0.7<y<1.3$, more preferably $0.8<y<1.2$, still more preferably $0.9<y<1.1$.

The complex oxide containing Mn in a compound of the formula (1) has a Mn content in the range of 0.00005 to 0.05 (molar ratio to 1 mol of magnesium in the formula). When the Mn content is in the range, good emission performance can be obtained. The lower limit of the Mn content is more preferably 0.0001, still more preferably 0.001.

The upper limit of the Mn content is more preferably 0.01, still more preferably 0.005.

For the x and y, the lower limit of x/y is preferably 1.5, more preferably 1.8 and the upper limit thereof is preferably 2.7, more preferably 2.2.

In the formula (2), x satisfies $0.1<x<1.05$, preferably $0.5<x<1.03$, more preferably $0.8<x<1.02$, still more preferably $0.9<x<1.01$.

In the formula (2), y satisfies $11.9<y\leq12$, preferably $11.901<y\leq12$, more preferably $11.905<y\leq12$, still more preferably $y=12$.

The complex oxide containing Mn in a compound of the formula (2) has a Mn content in the range of 0.000042 to 0.0083 (molar ratio to 1 mol of aluminum in the formula). When the Mn content is in the range, good emission performance can be obtained. The lower limit of Mn content is more preferably 0.00005, still more preferably 0.0001. The upper limit of the Mn content is more preferably 0.005, still more preferably 0.001.

In the formula (3), x satisfies $3.2\leq x\leq5.0$, preferably $3.3<x<4.7$, more preferably $3.4<x<4.6$, still more preferably $3.5<x<4.5$.

In the formula (3), y satisfies $1.9\leq y\leq2.1$, preferably $1.95<y<2.05$, more preferably $1.97<y<2.02$, still more preferably $y=2$.

The complex oxide containing Ce in a compound of the formula (3) has a Ce content in the range of 0.0005 to 0.05 (molar ratio to 1 mol of phosphorus in the formula). When the Ce content is in the range, good emission performance can be obtained. The lower limit of the Ce content is more preferably 0.0006, still more preferably 0.0007. The upper limit of the Ce content is more preferably 0.045, still more preferably 0.04.

The fluorescent zinc oxide may be any zinc oxide that emits light upon excitation by ultraviolet light. It is preferably zinc oxide with an oxygen defect obtained by reducing zinc oxide (ZnO). The zinc oxide with an oxygen defect is considered to be represented by the average composition formula $Zn_{1+z}O$ or $ZnO_{1-x}$.

When the complex oxides containing Mn or Ce in compounds of the formulas (1) to (3) and the fluorescent zinc oxide are excited by light in the near-ultraviolet to blue region, such as light having a wavelength of 200 nm to 400 nm, the phosphor containing a compound of the formula (1) shows an orange to red emission color, the phosphor containing a compound of the formula (2) shows an orange to red emission color, the phosphor containing a compound of the formula (3) shows a blue to green emission color, and the fluorescent zinc oxide shows a green emission color.

In the mixture which contains a phosphor (hereinafter referred to as a phosphor A) containing at least one selected from the group consisting of a complex oxide containing Mn in a compound of the formula (1) and a complex oxide containing Mn in a compound of the formula (2) and a phosphor (hereinafter referred to as a phosphor B) containing at least one selected from the group consisting of a complex oxide containing Ce in a compound of the formula (3) and a fluorescent zinc oxide, the mass ratio of the phosphor A to the phosphor B (phosphor A/phosphor B) is preferably 1/99 to 99/1, more preferably 5/95 to 60/40, still more preferably 35/65 to 45/55.

When the phosphor A contains both the complex oxide containing Mn in a compound of the formula (1) and the complex oxide containing Mn in a compound of the formula (2), the compounding ratio between the complex oxide containing Mn in a compound of the formula (1) and the complex oxide containing Mn in a compound of the formula (2) may be adjusted within such a range that the mass ratio of the phosphor A to the phosphor B can be in the above range.

Also when the phosphor B contains both the complex oxide containing Ce in a compound of the formula (3) and the fluorescent zinc oxide, as in the case of the phosphor A, the compounding ratio between the compound of the formula (3) and the fluorescent zinc oxide may be adjusted within such a range that the mass ratio of the phosphor A to the phosphor B can be in the above range.

When the phosphor A contains a compound of the formula (1), the phosphor A may contain one or two or more compounds of the formula (1). Similarly, the phosphor A may contain one or two or more compounds of the formula (2).

Similarly, the phosphor B may contain one or two or more compounds of the formula (3) and may contain one or two or more fluorescent zinc oxides.

The complex oxide containing Mn in a compound of the formula (1) and the complex oxide containing Mn in a compound of the formula (2) may be produced by any method. Exemplary methods include the methods disclosed in WO 2016/017372 (compound of the formula (1)) and the methods disclosed in WO 2015/166895 (compound of the formula (2)).

The complex oxide containing Ce in a compound of the formula (3) may be produced by any method. For example, it may be produced by mixing, at a predetermined ratio, a compound of Ce and compounds of elements to constitute the complex oxide containing Ce in a compound of the formula (3), and reduction-firing the mixture.

The fluorescent zinc oxide may be produced by any method. For example, it may be produced by adding a sulfur-containing compound to an oxygen-containing zinc compound (e.g., zinc oxide or zinc carbonate), followed by firing the mixture in a reducing atmosphere.

Alternatively, the complex oxides containing Mn or Ce in the compounds of the formulas (1) to (3) and the fluorescent zinc oxide may be produced with reference to the methods described in Examples below.

The phosphors contained in the cosmetic product of the present invention each preferably have a median size ($D_{50}$) of 0.1 to 20 μm. The phosphors having a $D_{50}$ in this range can have more sufficient emission intensity, and gives more comfortable feeling when applied to the skin. The phosphors having such a $D_{50}$ also provide UV protection ability and a soft focus effect. The $D_{50}$ of the phosphors is more preferably 0.5 to 15 μm, still more preferably 1 to 12 μm.

The median size ($D_{50}$) herein means a volume-based 50% cumulative particle size, and means a particle size that divides powder (particles) into two equal parts, one consisting of particles larger than the particle size and the other consisting of particles smaller than the particle size. The $D_{50}$ of the phosphors can be measured by the method described in Examples below.

The phosphors contained in the cosmetic product of the present invention each preferably have an internal quantum efficiency of 1% or higher upon excitation by excitation light having a wavelength of 365 nm. Such an internal quantum efficiency makes them useful as phosphors. The internal quantum efficiency is more preferably 20% or higher, still more preferably 25% or higher, particularly preferably 30% or higher, most preferably 35% or higher.

The internal quantum efficiency as used herein can be measured by the method described in Examples below.

The cosmetic product of the present invention preferably has a phosphor content of 0.1 to 20% by weight relative to the entire cosmetic product. When the phosphor content is within this range, the effects of the cosmetic product of the present invention can be more sufficiently exhibited without impairing the comfortable feeling and the uniformity of the cosmetic film. The phosphor content is more preferably 0.5 to 15% by weight relative to the entire cosmetic product.

The cosmetic product of the present invention preferably has a Eu component content of 1% by mass or less of the entire cosmetic product. Such a Eu component content makes the cosmetic product safer to be directly used on the human skin. The Eu component content is more preferably 0.8% by mass or less of the entire cosmetic product, still more preferably 0.5% by mass or less of the entire cosmetic product.

The Eu component content of the cosmetic product can be measured with the inductively coupled plasma (ICP) emission spectrometry described later.

The Eu component herein means elemental Eu and a compound of Eu.

The cosmetic product of the present invention preferably has an internal quantum efficiency of 1 to 40% upon excitation by excitation light having a wavelength of 365 nm.

As described below, the cosmetic product is prepared by mixing the two or more phosphors each containing an inorganic compound with other components, which may include a UV absorber or a color pigment.

However, UV absorbers absorb ultraviolet light and color pigments absorb visible light. Adding these components in large amounts prevents the phosphors from sufficiently absorbing ultraviolet light or visible light required for excitation, and thus prevents the phosphors from sufficiently exhibiting the above effects. For example, a fluorescent cosmetic product containing a large amount of a UV absorber may not give a natural white color under sunlight because the emission from the blue or green phosphor, which is excited by ultraviolet light, is insufficient whereas the emission from the red phosphor, which emits light even under visible light, is noticeable. With this respect, when the UV absorber and color pigment are added such that the internal quantum efficiency is 1 to 40% upon excitation of the cosmetic product by excitation light having a wavelength of 365 nm, the effects of the phosphors and the effects of the UV absorber and color pigment are exhibited in a balanced manner. The cosmetic product thus can have emission that makes it possible to more clearly feel the effectiveness of the effect of enhancing the three-dimensional appearance of the face under sunlight and the effect of moderating skin discoloration and a reduction in translucency.

The internal quantum efficiency upon excitation of the cosmetic product of the present invention by excitation light having a wavelength of 365 nm is more preferably 3 to 30%.

The internal quantum efficiency upon excitation of the cosmetic product by excitation light having a wavelength of 365 nm can be measured by the method described in Examples below.

The cosmetic product of the present invention contains the above two or more phosphors each containing an inorganic compound and other components. Examples of other component include, but not limited to, organic solvents, dispersants, and any aqueous components and oil components usually used in the cosmetic field. Specific examples thereof include oils; surfactants; moisturizers; higher alcohols; sequestrants; polymers (natural, semisynthetic, synthetic, or inorganic, water- or oil-soluble polymers); UV blocking agents; other drug components; various extracts; inorganic and organic pigments; inorganic and organic clay minerals and other various powders; inorganic and organic pigments treated with metallic soap or silicone; coloring materials such as organic dyes; preservatives; antioxidants; colorants; thickeners; pH adjusters; perfumes; cooling-sensation agents; astringents; disinfectants; and skin activators. The amounts of these components are not limited as long as they do not interfere with the effects of the present invention.

The oil is not limited, and examples thereof include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, perilla oil, soybean oil, arachis oil, tea seed oil, kaya oil, rice bran oil, Chinese tung oil, Japanese tung oil, jojoba oil, germ oil, triglycerin, glycerin trioctanoate, glycerin triisopalmitate, cacao butter, coconut oil, horse fat, palm oil, beef tallow, mutton tallow, palm kernel oil, lard, beef bone fat, Japan wax kernel oil, hydrogenated beef tallow, hydrogenated oils such as hydrogenated coconut oil and hydrogenated castor oil, neatsfoot oil, Japan wax, beeswax, candelilla wax, cotton wax, carnauba wax, bayberry wax, insect wax, spermaceti wax, montan wax, bran wax, lanolin, kapok wax, lanolin acetate, liquid lanolin, sugarcane wax, isopropyl lanolate, hexyl laurate, reduced lanolin, jojoba wax, hard lanolin, shellac wax, POE lanolin alcohol ether, POE lanolin alcohol acetate, POE cholesterol ether, polyethylene glycol lanolate, POE hydrogenated lanolin alcohol ether, liquid paraffin, ozokerite, pristane, paraffin, ceresin, squalene, vaseline, and microcrystalline wax.

Examples of the surfactant include lipophilic nonionic surfactants, hydrophilic nonionic surfactants, and other surfactants. The lipophilic nonionic surfactant is not limited, and examples thereof include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerin sorbitan penta-2-ethylhexylate, and diglycerin sorbitan tetra-2-ethylhexylate; glycerin polyglycerin fatty acids such as mono-cottonseed oil fatty acid glycerin, glycerin monoerucate, glycerin sesquioleate, glycerin monostearate, α,α'-glycerin oleate pyroglutamate, and glycerin monostearate malate; propylene glycol fatty acid esters such as propylene glycol monostearate; hydrogenated castor oil derivatives; and glycerin alkyl ethers.

The hydrophilic nonionic surfactant is not limited, and examples thereof include POE sorbitan fatty acid esters such as POE sorbitan monooleate, POE sorbitan monostearate, and POE sorbitan tetraoleate; POE sorbitol fatty acid esters such as POE sorbitol monolaurate, POE sorbitol monooleate, POE sorbitol pentaoleate, and POE sorbitol monostearate; POE glycerin fatty acid esters such as POE glycerin monostearate, POE glycerin monoisostearate, and POE glycerin triisostearate; POE fatty acid esters such as POE monooleate, POE distearate, POE dioleate, and ethylene glycol distearate; POE alkyl ethers such as POE lauryl ether, POE oleyl ether, POE stearyl ether, POE behenyl ether, POE 2-octyldodecyl ether, and POE cholestanol ether; POE alkyl phenyl ethers such as POE octyl phenyl ether, POE nonyl phenyl ether, and POE dinonyl phenyl ether; Pluaronic types such as Pluronic; POE/POP alkyl ethers such as POE/POP cetyl ether, POE/POP 2-decyltetradecyl ether, POE/POP monobutyl ether, POE/POP hydrogenated lanolin, and POE/POP glycerin ether; tetra-POE/tetra-POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester, and POE hydrogenated castor oil maleic acid; POE beeswax/lanolin derivatives such as POE sorbitol beeswax; alkanolamides such as coconut oil fatty acid diethanolamide, lauric acid monoethanolamide, and fatty acid isopropanol amide; POE propylene glycol fatty acid esters; POE alkylamines; POE fatty acid amides; sucrose fatty acid esters; POE nonylphenyl formaldehyde condensation products; alkyl ethoxy dimethylamine oxides; and trioleyl phosphoric acid.

Examples of other surfactants include anionic surfactants such as fatty acid soaps, higher-alkyl sulfuric ester salts, POE triethanolamine lauryl sulfate, and alkyl ether sulfuric ester salts; cationic surfactants such as alkyl trimethylammonium salts, alkyl pyridinium salts, alkyl quaternary ammonium salts, alkyl dimethylbenzyl ammonium salts, POE alkylamines, alkylamine salts, and polyamine fatty acid derivatives; and amphoteric surfactants such as imidazoline amphoteric surfactants and betaine surfactants.

The moisturizer is not limited, and examples thereof include xylitol, sorbitol, maltitol, chondroitin sulfate, hyaluronic acid, mucoitinsulfuric acid, caronic acid, atelocollagen, cholesteryl-12-hydroxystearate, sodium lactate, bile salts, dl-pyrrolidone carboxylate, short-chain soluble collagens, diglycerin (EO) PO adducts, *Rosa roxburghii* extract, yarrow extract, and melilot extract.

The higher alcohol is not limited, and examples thereof include linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerin ether (batyl alcohol), 2-decyltetradecynol, lanolin alcohol, cholesterol, phytosterol, hexyldodecanol, isostearyl alcohol, and octyldodecanol.

The sequestrant is not limited, and examples thereof include 1-hydroxyethane-1,1-diphosphonic acid, tetrasodium 1-hydroxyethane-1,1-diphosphonate, sodium citrate, sodium polyphosphate, sodium metaphosphate, gluconic acid, phosphoric acid, citric acid, ascorbic acid, succinic acid, and edetic acid.

The natural water-soluble polymer is not limited, and examples thereof include plant-derived polymers such as gum arabic, tragacanth gum, galactan, guar gum, carob gum, karaya gum, carrageenan, pectin, agar, quince seed (quince), algal colloid (algal extract), starch (rice, corn, potato, wheat), and glycyrrhizinic acid; microorganism-derived polymers such as xanthan gum, dextran, succinoglucan, and pullulan; and animal-derived polymers such as collagen, casein, albumin, and gelatin.

The semisynthetic water-soluble polymer is not limited, and examples thereof include starch polymers such as carboxymethyl starch and methyl hydroxypropyl starch; cellulose polymers such as methyl cellulose, nitro cellulose, ethyl cellulose, methyl hydroxypropyl cellulose, hydroxyethyl cellulose, cellulose sodium sulfate, hydroxypropyl cellulose, sodium carboxymethyl cellulose (CMC), crystalline cellulose, and cellulose powder; and alginate polymers such as sodium alginate and propylene glycol alginate.

The synthetic water-soluble polymer is not limited, and examples thereof include vinyl polymers such as polyvinyl alcohol, polyvinyl methyl ether, and polyvinyl pyrrolidone; polyoxyethylene polymers such as polyethylene glycol 20000, polyethylene glycol 40000, and polyethylene glycol 60000; copolymers such as polyoxyethylene-polyoxypropylene copolymers; acrylic polymers such as sodium polyacrylate, polyethylacrylate, and polyacrylamide; polyethyleneimine; and cationic polymers.

The inorganic water-soluble polymer is not limited, and examples thereof include bentonite, magnesium aluminum silicate (Veegum), laponite, hectorite, and silicic anhydride.

The UV blocking agent is not limited, and examples thereof include benzoic acid UV blocking agents such as paraaminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, and N,N-dimethyl PABA butyl ester; anthranilic acid UV blocking agents such as homomenthyl-N-acetyl anthranilate; salicylic acid UV blocking agents such as amyl salicylate, menthyl salicylate, homomenthyl salicylate, octyl salicylate, phenyl salicylate, benzyl salicylate, and p-isopropanol phenyl salicylate; cinnamic acid UV blocking agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glycerylmono-2-ethylhexanoyl-diparamethoxy cinnamate; benzophenone UV blocking agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotrialzole, 2-(2'-hydroxy-5'-t-octylphenyl)benzotriazole, 2-(2'-hydroxy-5'-methylphenyl) benzotriazole, dibenzalazine, dianisoylmethane, 4-methoxy-4'-t-butyldibenzoylmethane, and 5-(3,3-dimethyl-2-norbornylidene)-3-pentan-2-one.

Other components are not limited, and examples thereof include vitamins such as vitamin A oil, retinol, retinol palmitate, inositol, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), DL-α-tocopherol, DL-α-tocopherol acetate, pantothenic acid, and biotin; hormones such as estradiol and ethynyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor; sulfur, lysozyme chloride, and pyridoxine chloride.

The extracts are not limited, and examples thereof include Houttuynia *cordata* extract, Phellodendron bark extract, melilot extract, dead nettle extract, licorice extract, peony root extract, soapwort extract, luffa extract, cinchona extract, strawberry geranium extract, *sophora* root extract, *nuphar* extract, fennel extract, primrose extract, rose extract, rehmannia root extract, lemon extract, lithospermum root extract, aloe extract, calamus root extract, *eucalyptus* extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, *hamamelis* extract, placenta extract, thymic extract, silk extract, and licorice extract.

Examples of the powders include bright coloring pigments such as red oxide, yellow iron oxide, black iron oxide, mica titanium, iron oxide-coated mica titanium, and titanium oxide-coated glass flakes, inorganic powders such as those of mica, talc, kaolin, sericite, titanium dioxide, barium sulfate, and silica, and organic powders such as polyethylene powder, nylon powder, crosslinked polystyrene powder, cellulose powder, and silicone powder. Preferably, part or all of the powder component is subjected to a known hydrophobization treatment with a substance such as a silicone, a fluorine compound, a metallic soap, an oily agent, or an acyl glutamic acid salt for improvement of sensory characteristics and improvement of makeup retainability.

The cosmetic product of the present invention is not limited, and can be used in applications including: basic cosmetic products such as lotions, moisturizers, emulsions, essences, hand creams, body lotions, and body creams; powder foundations, liquid foundations, face powders, mousse powders, and concealers; makeup cosmetic products such as blushers, eye shadows, mascaras, eyeliners, eyebrow makeup products, topcoats, lipsticks, and makeup bases (the basic cosmetic products and makeup cosmetic products may or may not disclose that they have a sunscreen function (UV cut function)); sunscreen cosmetic products such as sunscreen emulsions and sunscreen creams; and makeup films for concealing blemishes, pimples, or scars. The cosmetic product of the present invention also can be used in multifunctional preparations that combine two or more of the functions of the above preparations in one preparation. These preparations can be produced by conventional methods.

The makeup film in the present invention means a cosmetic product applied to the skin to conceal scars on the skin or to obscure the appearance of blemishes, wrinkles, and pimples, in the cosmetic field, the medical field, and other fields. Makeup films usually contain a resin component.

The makeup film may be in any form. Examples of the form include film, tape, seal, and roll forms. The makeup film encompasses a makeup film provided with an adhesive.

The makeup film of the present invention contains phosphors and a resin. The resin may be appropriately selected according to the form and application of the makeup film. The resin may be a thermoplastic resin, a thermosetting resin, or a photocurable resin. Specific examples include epoxy resins, phenolic resins, polyphenylene sulfide (PPS) resins, polyester resins, polyamides, polyimides, maleimide resins, polystyrene, polyethylene, polypropylene, polyvinyl chloride, polyvinylidene chloride, fluororesins, polymethyl methacrylate, ethylene-vinyl acetate copolymer (EVA) resins, polycarbonates, polyurethanes, polyacetals, polyphenylene ether, polyetherimide, acrylonitrile-butadiene-styrene copolymer (ABS) resins, liquid crystal resins (LCP), silicone resins, and acrylic resins. These may be used alone or in combination of two or more thereof. Specific examples of the photocurable resin include acrylate compounds, methacrylate compounds, epoxy compounds, isocyanate compounds, thiol compounds, and silicone compounds polymerizable using a photopolymerization initiator.

The makeup film of the present invention may further contain other components if necessary. Each component may be used alone or in combination of two or more kinds thereof.

The makeup film of the present invention preferably has a thickness of 10 to 300 μm.

The sunscreen cosmetic product in the present invention means a cosmetic product used to protect the skin from ultraviolet light. Sunscreen cosmetic products usually contain a UV absorber and/or a UV scattering agent. The sunscreen cosmetic product may be in any form. Examples thereof include oil-in-water or water-in-oil emulsion forms and stick (solid) forms. The sunscreen cosmetic product encompasses a sunscreen cosmetic product having a makeup base function.

The makeup base in the present invention means a cosmetic product used to, for example, correct skin unevenness, correct skin color, improve the attachment and spread of makeup cosmetic products such as foundations, improve makeup finish and makeup durability, and protect the skin from ultraviolet light (makeup base having a sunscreen function). The makeup base may be in any form. Examples thereof include oil-in-water or water-in-oil emulsion forms, cream forms, and stick (solid) forms.

The foundation may be in any form. Examples thereof include solid, powder, oil-based stick, oil-in-water or water-in-oil emulsion, and cream forms.

The blusher and face powder also may be in any form. The blusher may be in a powder, cream, or stick form, for example. The face powder may be in a powder form, for example.

The method for applying makeup using the cosmetic product of the present invention is not limited. Examples thereof include: a method involving applying a makeup base to the skin and then applying the cosmetic product of the present invention; a method involving conditioning the skin with basic cosmetic products such as a lotion, an emulsion, and an essence, applying a makeup base and the like to the skin, and then applying the cosmetic product of the present invention.

The cosmetic product of the present invention is preferably applied last, over a base cosmetic product after the base cosmetic product is applied to the skin. Such a method of use of the cosmetic product of the present invention is also encompassed by the present invention. When applied over a base cosmetic product, the cosmetic product of the present invention can be uniformly applied over the skin surface. Additionally, sunscreen cosmetic products, makeup bases, foundations, and the like usually contain light absorbing materials (e.g., UV absorbers or color pigments) or light scattering materials (e.g., UV scattering agents or pearl pigments). Thus, applying these cosmetic products onto the phosphor-containing cosmetic product causes interference with part of ultraviolet light or visible light required for excitation of the phosphors, and also causes absorption of part of the emission from the phosphors. This may result in insufficient emission from the phosphors. In contrast, applying the cosmetic product of the present invention after applying the base cosmetic product to the skin enables the phosphors to sufficiently absorb ultraviolet light or visible light, resulting in more sufficient emission from the phosphors. Furthermore, since the phosphors contained in the cosmetic product of the present invention absorb part of ultraviolet light, the cosmetic product of the present invention also exhibits a sunscreen effect.

Thus, in a preferred embodiment of the present invention, the cosmetic product of the present invention is in a form selected from powder foundations, liquid foundations, face powders, eye shadows, and makeup films, among the above-mentioned forms. Since the foundations and face powders are used over a base cosmetic product, even when the base cosmetic product contains a UV absorber, the phosphors contained in the cosmetic product can sufficiently absorb ultraviolet light, and makes it possible to more sufficiently feel the effectiveness of the effect of enhancing the three-dimensional appearance of the face or the effect of moderating skin discoloration and a reduction in translucency. The form is more preferably a face powder.

When the cosmetic product of the present invention is used in a makeup film form, it is preferably attached last, over a base cosmetic product after the base cosmetic product is applied to the skin. Such a method of use of the cosmetic product of the present invention is also encompassed by the present invention. When attached over a base cosmetic product, the cosmetic product of the present invention can be uniformly attached over the skin surface. A foundation and the like may be applied near the boundary between the makeup film and the skin to visually blur the boundary and reduce visual discomfort.

The base cosmetic product that can be used before applying the cosmetic product of the present invention is not limited, and may be one commonly commercially available. Examples of the type of the base cosmetic product include: emulsion compositions such as water-in-oil emulsion compositions and oil-in-water emulsion compositions; and oil compositions. Examples of the form of the base cosmetic product include cream, liquid, gel, and solid forms.

EXAMPLES

The present invention will be described in detail with reference to examples below. The present invention should not be limited to these examples.

The following methods were used for the measurement of the $D_{50}$ and the composition (element contents) of the phosphors synthesized in Synthesis Examples 1 to 4 and the measurement of the Eu content of the cosmetic products produced in the examples and the comparative examples.

<Average Particle Size $D_{50}$>

The average particle size $D_{50}$ of each of the phosphors synthesized in Synthesis Examples 1 to 4 was measured as follows using a laser diffraction/scattering particle size analyzer (available from Nikkiso Co., Ltd., model Microtrac MT3000).

Specifically, 0.1 g of a sample was sufficiently dispersed in 60 mL of a 0.025 wt % aqueous solution of sodium hexametaphosphate by an ultrasonic homogenizer (US-600, available from NISSEI Corporation). The suspension thus prepared was used as a test sample. The $D_{50}$ was measured under the following conditions: a dispersion medium refractive index of 1.33 (0.025 wt % aqueous solution of sodium hexametaphosphate); a test sample refractive index of 2.15 for magnesium titanate manganese phosphor, 1.81 for calcium aluminate manganese phosphor, 1.64 for calcium phosphate cerium phosphor, or 2.00 for fluorescent zinc oxide; a flow rate of 50%; three minutes of ultrasonic dispersion; and a transmittance of 80 to 95%.

<Composition (Element Contents) and Eu Content>

The element contents in each powder were determined with an inductively coupled plasma (ICP) emission spectrometer (available from SII, ICP SPS3100) by a calibration curve method using scandium (Sc) as an internal standard. The measurement sample was prepared by dissolving the powder in hydrochloric acid. For insoluble powders, the measurement sample was prepared by an alkali fusion method using lithium tetraborate.

The following methods were used for the identification of the crystalline structure, the identification of the composition formula, and the measurement of the internal quantum efficiency of the phosphors synthesized in Synthesis Examples 1 to 4.

<Identification of Crystalline Structure>

A powder X-ray diffraction pattern (also referred to simply as an X-ray diffraction pattern) was used. The measurement was performed using RINT-UltimaIII available from Rigaku Corporation with parallel optics (long slit: 200 mm, opening angle: 0.057°) under the conditions of a step width of 0.02° and a measurement range of 2θ=1.6 to 70°.

The details of the measurement were as follows.

—Analysis Conditions—

Device: RINT-UltimaIII available from Rigaku Corporation
Source: CuKα
Voltage: 50 kV
Current: 300 mA
Sample rotational speed: 60 rpm
Divergence slit: 1.00 mm
Divergence height limiting slit: 10 mm
Long slit: 200 mm, opening angle 0.057°
Scattering slit: open
Receiving slit: open
Scan mode: FT
Counting time: 2.0 seconds
Step width: 0.0200°
Scan axis: 2θ/θ
Scan range: 1.6000 to 70.0000°
Number of scans: 1

<Identification of Composition Formula>

The composition formula of each phosphor was identified using the JCPDS card. The JCPDS card is a collection of peak profiles of various substances determined by X-ray diffractometry.

Magnesium titanate manganese phosphor: $Mg_2TiO_4$, JCPDS card 00-025-1157

Calcium aluminate manganese phosphor: $CaAl_{12}O_{19}$, JCPDS card 00-038-0470

Calcium phosphate cerium phosphor: $Ca_4(PO_4)_2O$, JCPDS card 00-025-1137

Fluorescent zinc oxide: ZnO, JCPDS card 00-036-1451

<Internal Quantum Efficiency>

The internal quantum efficiency of each powder (phosphor) was measured using QE-2000 (available from Otsuka Electronics Co., Ltd.).

The excitation wavelength was 365 nm and the measurement was performed in 5 nm steps. The details of the measurement were as follows.

Each powder (phosphor) was fed into a special holder and put into a quantum efficiency measurement system (QE-2000, available from Otsuka Electronics Co., Ltd). The emission spectrum was obtained in 5 nm steps at an excitation wavelength of 365 nm. From the obtained emission spectrum of the sample, an integrated value (L) of the emission spectrum in the wavelength range of 352 to 378 nm and an integrated value (E) of the emission spectrum in the wavelength range of 390 to 750 nm were determined. Subsequently, barium sulfate powder was fed into the special holder and put into the measurement device. The emission spectrum was obtained in 5 nm steps at an excitation wavelength of 365 nm. From the obtained emission spectrum of the barium sulfate, an integrated value (R) of the emission spectrum in the wavelength range of 352 to 378 nm was determined.

The internal quantum efficiency was calculated from the obtained L, E and R using the following equation.

$$\text{Internal quantum efficiency}=100\times E/(R-L)$$

Synthesis Example 1 (Synthesis of Magnesium Titanate Manganese Phosphor)

An amount of 1396 g of basic magnesium carbonate (available from Konoshima Chemical Co., Ltd., GP-30N, Mg content 26.1% by weight), 3.65 g of manganese carbonate (available from Chuo Denki Kogyo Co., Ltd., purity 94.6%), and 603 g of titanium oxide (available from Sakai Chemical Industry Co., Ltd., A-120, purity 99.0%) were weighed into ion-exchanged water. They were sufficiently mixed using a bead mill. The obtained mixed slurry was dried by evaporation to give firing precursor powder. Subsequently, the firing precursor powder was placed in an alumina crucible. The powder was heated to 1250° C. at 200° C./hour in an air atmosphere, held at the temperature for 10 hours, and then cooled to room temperature at 200° C./hour. This was followed by sufficient pulverization in ion-exchanged water using a planetary ball mill. The resulting pulverization slurry was dried at 130° C. for 12 hours. The obtained solid product was heated to 600° C. at 200° C./hour in an air atmosphere, held at the temperature for 24 hours, and then cooled to room temperature at 200° C./hour, whereby a magnesium titanate manganese phosphor was obtained. The phosphor was represented by the composition formula $Mg_2Ti_{0.996}O_{3.992}$, and had a Mn content of 0.002 mol relative to 1 mol of magnesium. The phosphor had a $D_{50}$ of 1.2 μm and an internal quantum efficiency of 75%.

Synthesis Example 2 (Synthesis of Calcium Aluminate Manganese Phosphor)

Calcium carbonate (available from Sakai Chemical Industry Co., Ltd., CWS-20, 5.21 g), manganese carbonate (available from Chuo Denki Kogyo Co., Ltd., 0.06 g), and aluminum oxide (available from Iwatani Chemical Industry Co., Ltd., RG-40, 31.9 g) were weighed into ion-exchanged water. They were sufficiently mixed using a planetary ball mill. The mixed slurry was dried at 130° C. by evaporation, and the resulting solid product was crushed in a mortar to give firing precursor powder. Subsequently, 15 g of the firing precursor powder was placed in an alumina crucible. The powder was heated to 1300° C. at 200° C./hour in an air atmosphere, held at the temperature for three hours, then cooled to room temperature at 200° C./hour, whereby a calcium aluminate manganese phosphor was obtained. The phosphor was represented by the composition formula $Ca_{0.99}Al_{11.96}O_{18.93}$, had a Mn content of 0.00083 mol relative to 1 mol of aluminum. The phosphor had a $D_{50}$ of 7.4 μm and an internal quantum efficiency of 51%.

Synthesis Example 3 (Synthesis of Calcium Phosphate Cerium Phosphor)

An amount of 20.35 g of calcium carbonate (available from Sakai Chemical Industry Co., Ltd., CWS-20), 0.17 g of cerium oxide (available from Shin-Etsu Chemical Co., Ltd.), 11.45 g of ammonium phosphate (available from Yoneyama Chemical Industry Co., Ltd.) were weighed into ion-exchanged water. They were sufficiently mixed using a planetary ball mill. Subsequently, the mixture was placed in an alumina crucible. The mixture was heated to 850° C. at 200° C./hour in an air atmosphere, held at the temperature for three hours, and then cooled at 200° C./hour. The resulting fired powder was sufficiently mixed and pulverized using a planetary ball mill. The pulverization slurry was dried overnight in a drier at 130° C. to give dried powder. The dried powder was then placed in an alumina crucible and heated to 1400° C. at 200° C./hour in a nitrogen atmosphere containing 3% by volume hydrogen, held at the temperature for eight hours, and cooled at 200° C./hour. The fired powder was pulverized using a planetary ball mill, whereby a calcium phosphate cerium phosphor was obtained. The phosphor was represented by the composition formula $Ca_{4.08}P_2O_{9.08}$, and had a Ce content of 0.01 mol relative to 1 mol of phosphorus. The phosphor had a $D_{50}$ of 5.1 μm and an internal quantum efficiency of 49%.

Synthesis Example 4 (Synthesis of Fluorescent Zinc Oxide) Example 1

An amount of 20 g of zinc oxide (available from Sakai Chemical Industry Co., Ltd., fine zinc oxide), 0.0179 g of zinc sulfide (available from Sakai Chemical Industry Co., Ltd., RAK-T), and 0.0105 g of sodium hydrogen carbonate (available from Kanto Chemical Co., Inc., guaranteed reagent for JIS) were weighed and well dry-mixed over 30 minutes. All the obtained raw material powder mixture was put in an alumina crucible, heated to 850° C. at 200° C./hour in a 1% by volume $H_2/N_2$ atmosphere, held at the temperature for two hours, and then cooled at 200° C./hour.

The resulting fired product was crushed in a mortar and all the crushed product was placed in an alumina crucible. The crushed product was then heated to 700° C. at 200° C./hour in an air atmosphere, held at the temperature for one hour, and then cooled at 200° C./hour. The resulting powder was subjected to washing with water and filtration. The resulting cake was dried in a dryer at 130° C. overnight, whereby fluorescent zinc oxide was obtained.

The phosphor had a $D_{50}$ of 3.5 μm and an internal quantum efficiency of 35%.

Examples 1 to 10 and Comparative Examples 1 to 6

(Production of Cosmetic Products)

Cosmetic products 1 to 10 and Comparative cosmetic products 1 to 6 were produced by the following production methods using the phosphors synthesized in Synthesis Examples 1 to 4 and other components in proportions shown in Table 1.

[Production Method]

Examples 1 to 9 and Comparative Examples 1 to 6

Of the phosphors and other components to be used, powders were mixed using a Henschel Mixer. To the mixture was added a component serving as an oil component, followed by mixing. Then, 0.8 g of the obtained powdery mixture was weighed into a mold having diameter of 20 mmφ and held for 30 seconds at a pressure of 200 kgf/cm$^2$ using a press machine, whereby a cosmetic product (solid foundation) was obtained.

Example 10

The phosphors were added to an ethylene-vinyl acetate copolymer (available from Dow-Mitsui Polychemicals Co., Ltd., EVAFLEX EV360, also referred to as "EVA resin"). They were fed into a resin kneader (available from Toyo Seiki Seisaku-Sho, Ltd., Labo Plasto Mill) and kneaded for 20 minutes at a temperature of 90° C. and a rotor rotational rate of 60 rpm, whereby a resin composition was obtained. The resin composition was pressed using a press machine (available from Toyo Seiki Seisaku-Sho, Ltd., Mini Test Press MP-WNH) at a temperature of 110° C. under the following pressurizing conditions: 3 MPa×5 minutes, 5 MPa×3 minutes, and 10 MPa×2 minutes (in the stated order). The resin composition was then cooled to room temperature, whereby a cosmetic product (makeup film) was obtained. The obtained film had a thickness of 260 μm.

All the materials used in the cosmetic products were of cosmetic grade.

For the cosmetic products obtained in Examples 1 to 10 and Comparative Examples 1 to 6, the chromaticity and the emission spectrum at 365 nm excitation light were measured by the following methods, and the half width in the range of 400 to 530 nm, $I_2/I_1$, and $I_2/I_3$ were determined. The internal quantum efficiency of the cosmetic products was also measured. Further, the cosmetic products were illuminated with 365 nm ultraviolet light using Handy UV Lamp (available from AS ONE Corporation, LUV-16), and their fluorescent emission colors were visually observed. Further, the translucent sheen, the uniformity of the cosmetic film, and the effect of enhancing the three-dimensional appearance were evaluated by the following methods. Table 1 shows the results.

Figure 2:
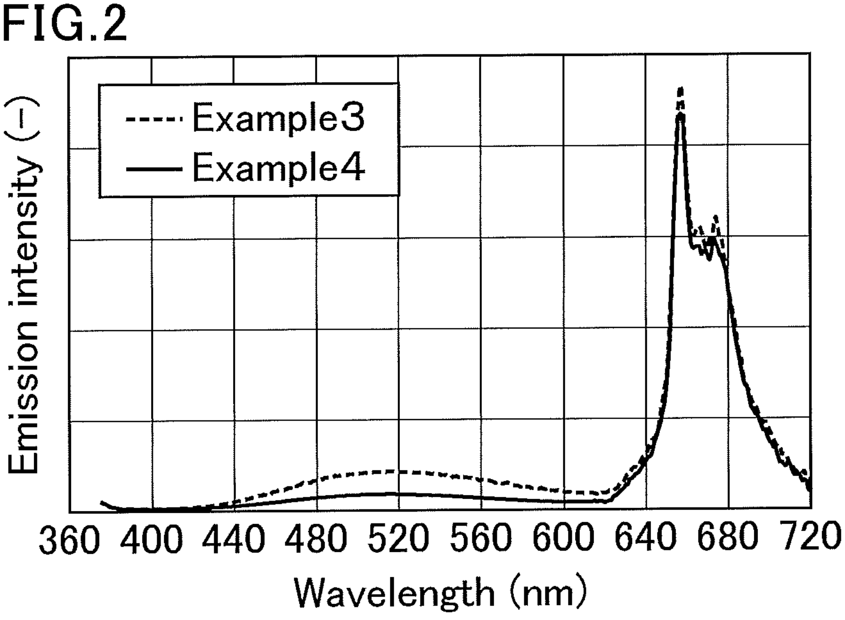
FIG. 2 shows the emission spectrum measurement results of Cosmetic products 3 and 4 obtained in Examples 3 and 4.
Figure 3:
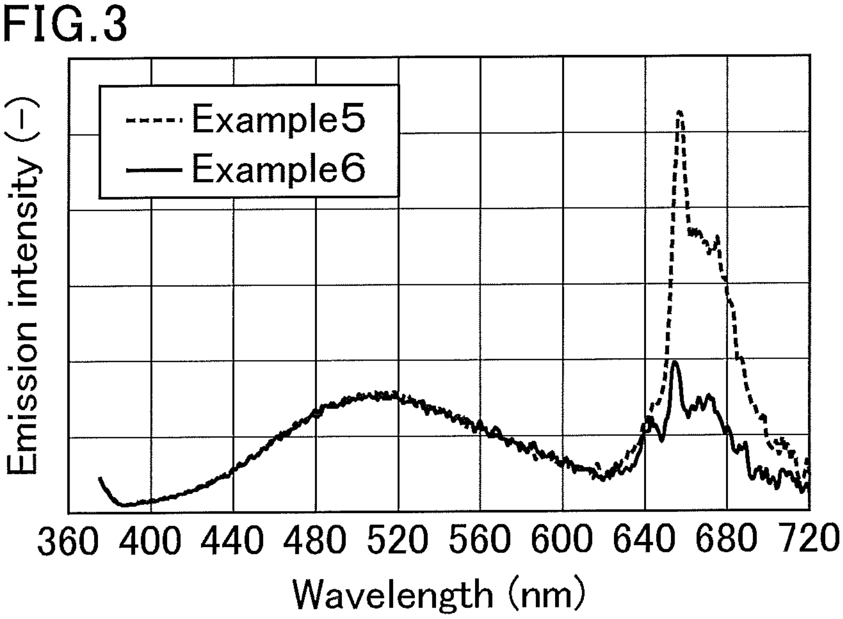
FIG. 3 shows the emission spectrum measurement results of Cosmetic products 5 and 6 obtained in Examples 5 and 6.
Figure 4:
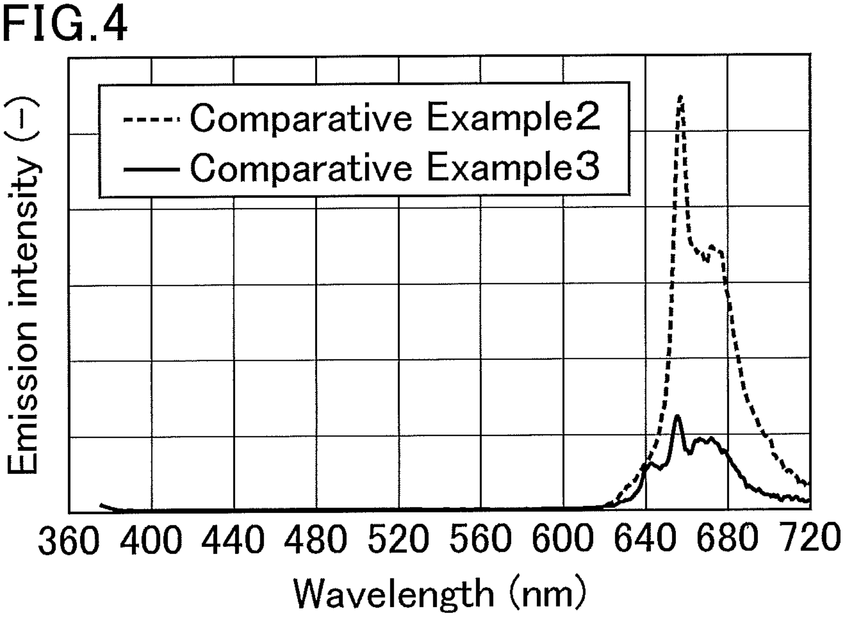
FIG. 4 shows the emission spectrum measurement results of Comparative cosmetic products 2 and 3 obtained in Comparative Examples 2 and 3.
Figure 5:
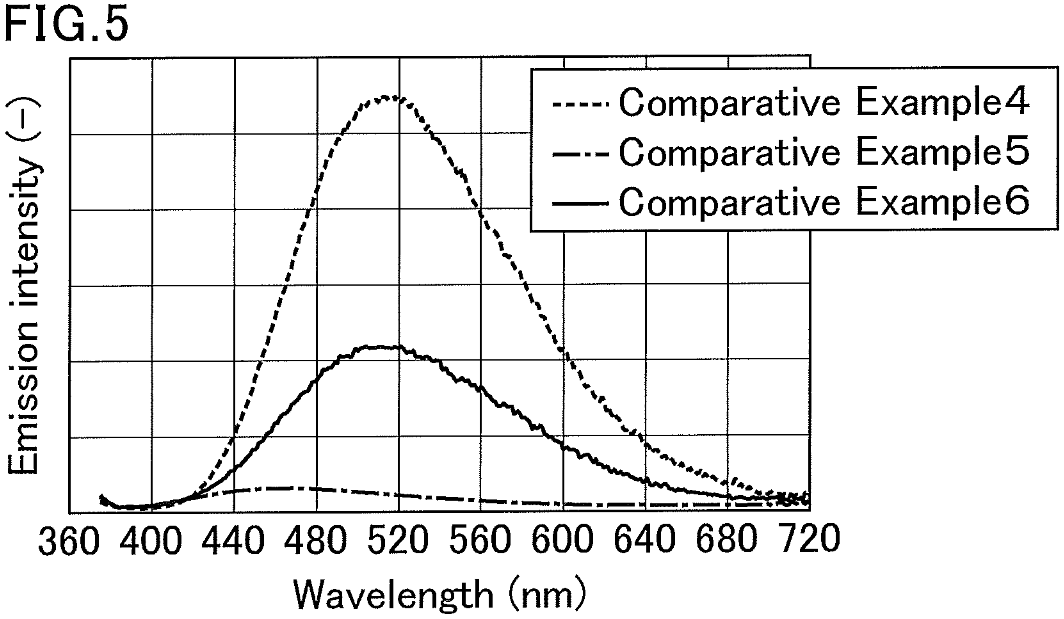
FIG. 5 shows the emission spectrum measurement results of Comparative cosmetic products 4, 5, and 6 obtained in Comparative Examples 4, 5, and 6.
Figure 6:
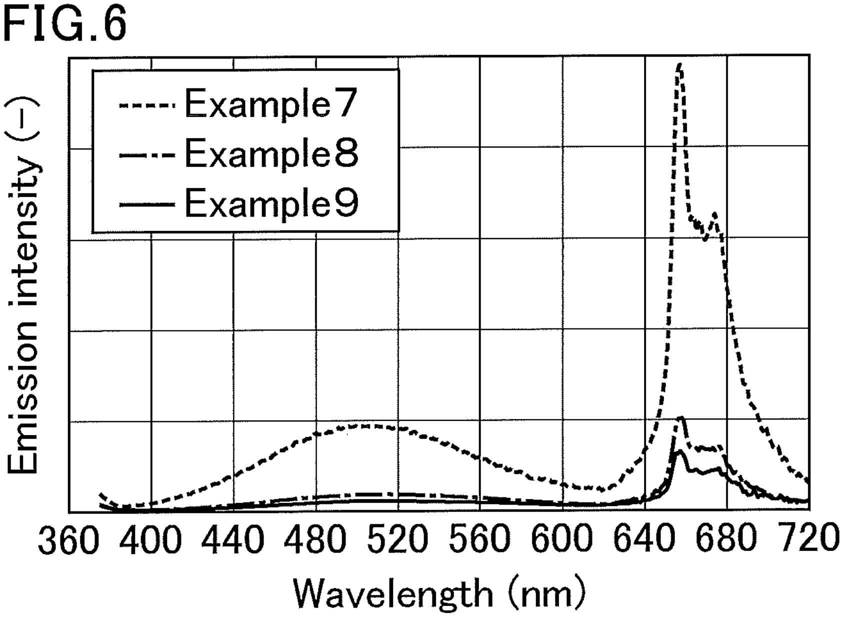
FIG. 6 shows the emission spectrum measurement results of Cosmetic products 7 to 9 obtained in Examples 7 to 9.
Figure 7:
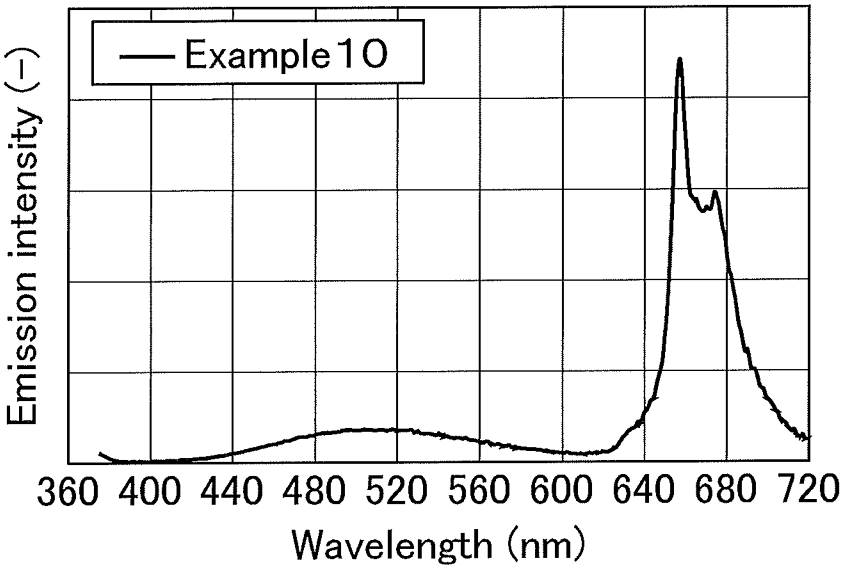
FIG. 7 shows the emission spectrum measurement results of Cosmetic product 10 obtained in Example 10.

FIG. 1 shows the emission spectrum measurement results of Cosmetic products 1 and 2 obtained in Examples 1 and 2. FIG. 2 shows the emission spectrum measurement results of Cosmetic products 3 and 4 obtained in Examples 3 and 4. FIG. 3 shows the emission spectrum measurement results of Cosmetic products 5 and 6 obtained in Examples 5 and 6. FIG. 4 shows the emission spectrum measurement results of Comparative cosmetic products 2 and 3 obtained in Comparative Examples 2 and 3. FIG. 5 shows the emission spectrum measurement results of Comparative cosmetic products 4, 5, and 6 obtained in Comparative Examples 4, 5, and 6. FIG. 6 shows the emission spectrum measurement results of Cosmetic products 7 to 9 obtained in Examples 7 to 9. FIG. 7 shows the emission spectrum measurement results of Cosmetic product 10 obtained in Example 10.

The Eu content of the cosmetic products obtained in Examples 1 to 10 and Comparative Examples 1 to 6 was measured by the above inductively coupled plasma (ICP) emission spectrometry. All the cosmetic products had a Eu content of 1 ppm or less.

[Chromaticity (x,y) and Emission Spectrum]

The emission spectrum was measured using FP-8600 available from Jasco Corporation. The excitation wavelength was 365 nm. The fluorescent integrating sphere was ISF-834 model and the sensitivity was set at Medium. The CIE chromaticity coordinates of the emission color was calculated from the color obtained by applying the results of the emission spectrum measurement to the CIE chromaticity coordinates.

[Internal Quantum Efficiency]

The internal quantum efficiency of each powder and the makeup film (cosmetic product) was measured using QE-2000 (available from Otsuka Electronics Co., Ltd.) by the same method as for the internal quantum efficiency of the phosphors.

[Translucent Sheen, Uniformity of Cosmetic Film, and Effect of Enhancing Three-Dimensional Appearance]

Ten panelists performed sensory evaluation in four grades: 3: Very good; 2: Good; 1: Fair; and 0: Poor. The translucent sheen, the uniformity of the cosmetic film, and the effect of enhancing three-dimensional appearance were each evaluated based on the average of the ten panelists according to the criteria below. The cosmetic products (foundations) were applied to the entire face. The cosmetic product (makeup film) was applied to the cheek of the face. The panelists visually performed the sensory evaluation of the translucent sheen, the uniformity of the cosmetic film, and the effect of enhancing three-dimensional appearance on the applied cosmetic films under sunlight in the daytime on a sunny day. In particular, the effect of enhancing the three-dimensional appearance was evaluated from varied observation angles. For each evaluation item, the cosmetic products were compared to the cosmetic product of Comparative Example 1 and evaluated according to the following criteria. The results were evaluated based on the average point of the ten panelists according to the following criteria.

Very good: The average point of ten panelists was greater than 2 and not greater than 3.

Good: The average point of ten panelists was greater than 1 and not greater than 2.

Poor: The average point of ten panelists was 0 to 1.

TABLE 1

| | | | Formulation (wt %) | | | | |
|---|---|---|---|---|---|---|---|
| | | | Example 1 | Example 2 | Example 3 | Example 4 | Example 5 |
| Components | Phorphor obtained in Synthesis Example 1 | Magnesium titanate manganese | 3.8 | 0.5 | 9.0 | 9.5 | 1.9 |
| | Phorphor obtained in Synthesis Example 2 | Calcium aluminate manganese | 0 | 0 | 0 | 0 | 1.9 |
| | Phorphor obtained in Synthesis Example 3 | Calcium phosphate cerium | 5.6 | 9.5 | 0 | 0 | 5.6 |
| | Phorphor obtained in Synthesis Example 4 | Fluorescent zinc oxide | 0.6 | 0 | 1.0 | 0.5 | 0.6 |
| | Mica*1 | | 26.6 | 26.6 | 26.6 | 26.6 | 26.6 |
| | Sericite*2 | | 31.9 | 31.9 | 31.9 | 31.9 | 31.9 |
| | Flake-shaped barium sulfate*3 | | 12.8 | 12.8 | 12.8 | 12.8 | 12.8 |
| | Spherical silicone*4 | | 6.9 | 6.9 | 6.9 | 6.9 | 6.9 |
| | Titanium oxide*5 | | 0.79 | 0.79 | 0.79 | 0.79 | 0.79 |
| | Yellow iron oxide*6 | | 0.12 | 0.12 | 0.12 | 0.12 | 0.12 |
| | Red iron oxide*7 | | 0.04 | 0.04 | 0.04 | 0.04 | 0.04 |
| | Metallic soap*8 | | 1.0 | 1.0 | 1.0 | 1.0 | 1.0 |
| | Non-volatile silicone oil*9 | | 9.9 | 9.9 | 9.9 | 9.9 | 9.9 |
| | Resin*10 | | 0 | 0 | 0 | 0 | 0 |
| Properties | Emission at 365 nm excitation | Chromaticity of emission color CIEx | 0.35 | 0.37 | 0.41 | 0.49 | 0.32 |
| | | Chromaticity of emission color CIEy | 0.38 | 0.27 | 0.39 | 0.35 | 0.39 |
| | | Intensity ratio $I_2/I_1$ | 6.0 | 21.6 | 11.3 | 25.6 | 3.6 |
| | | Intensity ratio $I_2/I_3$ | 5.6 | 13.2 | 10.9 | 24.2 | 3.3 |
| | | Half width of emission peak in the range of 400 to 530 nm (nm) | 140 | 137 | 134 | 133 | 129 |
| | | Internal quantum efficiency of cosmetic product (%) | 5.3 | 2.5 | 10.5 | 9.1 | 4.5 |
| | | Fluorescent emission color | White | Violet | Pale orange | Orange | White |
| | Sensary evaluation | Translucent sheen | Very good | Good | Very good | Good | Very good |
| | | Uniformity of cosmetic film | Very good | Very good | Very good | Very good | Very good |
| | | Effect of enhancing three-dimensional appearance | Very good | Good | Very good | Good | Very good |

| | | | Formulation (wt %) | | | | |
|---|---|---|---|---|---|---|---|
| | | | Example 6 | Example 7 | Example 8 | Example 9 | Example 10 |
| Components | Phorphor obtained in Synthesis Example 1 | Magnesium titanate manganese | 0 | 3.8 | 3.8 | 3.8 | 0.95 |
| | Phorphor obtained in Synthesis Example 2 | Calcium aluminate manganese | 3.8 | 0 | 0 | 0 | 0 |
| | Phorphor obtained in Synthesis Example 3 | Calcium phosphate cerium | 5.6 | 5.6 | 5.6 | 5.6 | 0 |
| | Phorphor obtained in Synthesis Example 4 | Fluorescent zinc oxide | 0.6 | 0.6 | 0.6 | 0.6 | 0.05 |
| | Mica*1 | | 26.6 | 26.9 | 26.3 | 25.8 | 0 |
| | Sericite*2 | | 31.9 | 32.3 | 31.6 | 30.9 | 0 |
| | Flake-shaped barium sulfate*3 | | 12.8 | 12.9 | 12.7 | 12.4 | 0 |
| | Spherical silicone*4 | | 6.9 | 7.0 | 6.8 | 6.7 | 0 |
| | Titanium oxide*5 | | 0.79 | 0 | 1.6 | 3.1 | 0 |
| | Yellow iron oxide*6 | | 0.12 | 0 | 0.23 | 0.46 | 0 |
| | Red iron oxide*7 | | 0.04 | 0 | 0.08 | 0.15 | 0 |
| | Metallic soap*8 | | 1.0 | 1.0 | 1.0 | 1.0 | 0 |
| | Non-volatile silicone oil*9 | | 9.9 | 10.0 | 9.7 | 9.6 | 0 |
| | Resin*10 | | 0 | 0 | 0 | 0 | 99 |
| Properties | Emission at 365 nm excitation | Chromaticity of emission color CIEx | 0.30 | 0.32 | 0.34 | 0.36 | 0.40 |
| | | Chromaticity of emission color CIEy | 0.40 | 0.37 | 0.39 | 0.38 | 0.37 |
| | | Intensity ratio $I_2/I_1$ | 1.3 | 5.7 | 5.7 | 5.9 | 12.6 |
| | | Intensity ratio $I_2/I_3$ | 1.2 | 5.2 | 5.4 | 5.7 | 11.9 |

TABLE 1-continued

| | | | | | | | |
|---|---|---|---|---|---|---|---|
| | | Half width of emission peak in the range of 400 to 530 nm (nm) | 135 | 136 | 146 | 164 | 115 |
| | | Internal quantum efficiency of cosmetic product (%) | 3.1 | 22.2 | 2.5 | 1.5 | 5.7 |
| | | Fluorescent emission color | Pale green | White | White | White | White |
| | Sensary evaluation | Translucent sheen | Good | Very good | Good | Good | Good |
| | | Uniformity of cosmetic film | Very good | Very good | Very good | Very good | Good |
| | | Effect of enhancing three-dimensional appearance | Good | Very good | Good | Good | Good |

| | | | Formulation (wt %) | | | |
|---|---|---|---|---|---|---|
| | | | Comparative Example 1 | Comparative Example 2 | Comparative Example 3 | Comparative Example 4 |
| Components | Phorphor obtained in Synthesis Example 1 | Magnesium titanate manganese | 0 | 10 | 0 | 0 |
| | Phorphor obtained in Synthesis Example 2 | Calcium aluminate manganese | 0 | 0 | 10 | 0 |
| | Phorphor obtained in Synthesis Example 3 | Calcium phosphate cerium | 0 | 0 | 0 | 0 |
| | Phorphor obtained in Synthesis Example 4 | Fluorescent zinc oxide | 0 | 0 | 0 | 10 |
| | Mica*1 | | 29.6 | 26.6 | 26.6 | 26.6 |
| | Sericite*2 | | 35.5 | 31.9 | 31.9 | 31.9 |
| | Flake-shaped barium sulfate*3 | | 14.2 | 12.8 | 12.8 | 12.8 |
| | Spherical silicone*4 | | 7.7 | 6.9 | 6.9 | 6.9 |
| | Titanium oxide*5 | | 0.88 | 0.79 | 0.79 | 0.79 |
| | Yellow iron oxide*6 | | 0.13 | 0.12 | 0.12 | 0.12 |
| | Red iron oxide*7 | | 0.04 | 0.04 | 0.04 | 0.04 |
| | Metallic soap*8 | | 1.1 | 1.0 | 1.0 | 1.0 |
| | Non-volatile silicone oil*9 | | 10.9 | 9.9 | 9.9 | 9.9 |
| | Resin*10 | | 0 | 0 | 0 | 0 |
| Properties | Emission at 365 nm excitation | Chromaticity of emission color CIEx | — | 0.66 | 0.56 | 0.28 |
| | | Chromaticity of emission color CIEy | — | 0.27 | 0.29 | 0.45 |
| | | Intensity ratio $I_2/I_1$ | — | 127 | 25.1 | 0.3 |
| | | Intensity ratio $I_2/I_3$ | — | 230 | 44.8 | 0.3 |
| | | Half width of emission peak in the range of 400 to 530 nm (nm) | — | * | * | 125 |
| | | Internal quantum efficiency of cosmetic product (%) | — | 10.8 | 2.5 | 18.0 |
| | | Fluorescent emission color | — | Red | Pink | Green |
| | Sensary evaluation | Translucent sheen | Poor | Poor | Poor | Poor |
| | | Uniformity of cosmetic film | Good | Good | Good | Good |
| | | Effect of enhancing three-dimensional appearance | Poor | Poor | Poor | Poor |

| | | | Formulation (wt %) | |
|---|---|---|---|---|
| | | | Comparative Example 5 | Comparative Example 6 |
| Components | Phorphor obtained in Synthesis Example 1 | Magnesium titanate manganese | 0 | 0 |
| | Phorphor obtained in Synthesis Example 2 | Calcium aluminate manganese | 0 | 0 |
| | Phorphor obtained in Synthesis Example 3 | Calcium phosphate cerium | 10 | 8 |
| | Phorphor obtained in Synthesis Example 4 | Fluorescent zinc oxide | 0 | 2 |
| | Mica*1 | | 26.6 | 26.6 |
| | Sericite*2 | | 31.9 | 31.9 |
| | Flake-shaped barium sulfate*3 | | 12.8 | 12.8 |
| | Spherical silicone*4 | | 6.9 | 6.9 |
| | Titanium oxide*5 | | 0.79 | 0.79 |
| | Yellow iron oxide*6 | | 0.12 | 0.12 |
| | Red iron oxide*7 | | 0.04 | 0.04 |
| | Metallic soap*8 | | 1.0 | 1.0 |
| | Non-volatile silicone oil*9 | | 9.9 | 9.9 |
| | Resin*10 | | 0 | 0 |
| Properties | Emission at 365 nm excitation | Chromaticity of emission color CIEx | 0.24 | 0.28 |
| | | Chromaticity of emission color CIEy | 0.27 | 0.43 |
| | | Intensity ratio $I_2/I_1$ | 0.6 | 0.3 |
| | | Intensity ratio $I_2/I_3$ | 0.4 | 0.3 |
| | | Half width of emission peak in the range of 400 to 530 nm (nm) | 139 | 132 |
| | | Internal quantum efficiency of cosmetic product (%) | 1.9 | 7.5 |
| | | Fluorescent emission color | Blue | Bluish green |

TABLE 1-continued

| | | | |
|---|---|---|---|
| Sensary evaluation | Translucent sheen | Poor | Good |
| | Uniformity of cosmetic film | Good | Good |
| | Effect of enhancing three-dimensional appearance | Poor | Poor |

In Table 1, "*" in the measurement results of the half width of the emission peak in the range of 400 to 530 nm means that no emission peak was observed in the range of 400 to 530 nm.

In Table 1, the components marked with *1 to *9 were listed below.

*1: Y-2300X (available from Yamaguchi Mica Co., Ltd.)
*2: FSE (available from Sanshin Mining Ind. Co., Ltd.)
*3: Flake-shaped barium sulfate-H (available from Sakai Chemical Industry Co., Ltd.)
*4: KSP-105 (available from Shin-Etsu Chemical Co., Ltd.)
*5: R-3LD (available from Sakai Chemical Industry Co., Ltd.)
*6: Yellow iron oxide (available from PINOA Co., Ltd.)
*7: Red iron oxide (available from PINOA Co., Ltd.)
*8: JPM-100 (available from Sakai Chemical Industry Co., Ltd.)
*9: KF-96-100cs (available from Shin-Etsu Chemical Co., Ltd.)
*10: EVAFLEX EV360 (available from DuPont-Mitsui Polychemicals Co., Ltd.)

Example 11 and Comparative Example 7

[Spectral Reflectance Measurement with Applied Cosmetic Product]

The skin spectral reflectance before and after the application of the cosmetic product of Example 1 was measured. About 30 mg of a commercially available base cosmetic product was applied to a urethane elastomer (BIOSKIN, available from Beaulax) having feel and texture similar to those of the human skin, such that a circle of the base cosmetic product with a diameter of about 4 cm was formed (Test Example 1).

Figure 8:
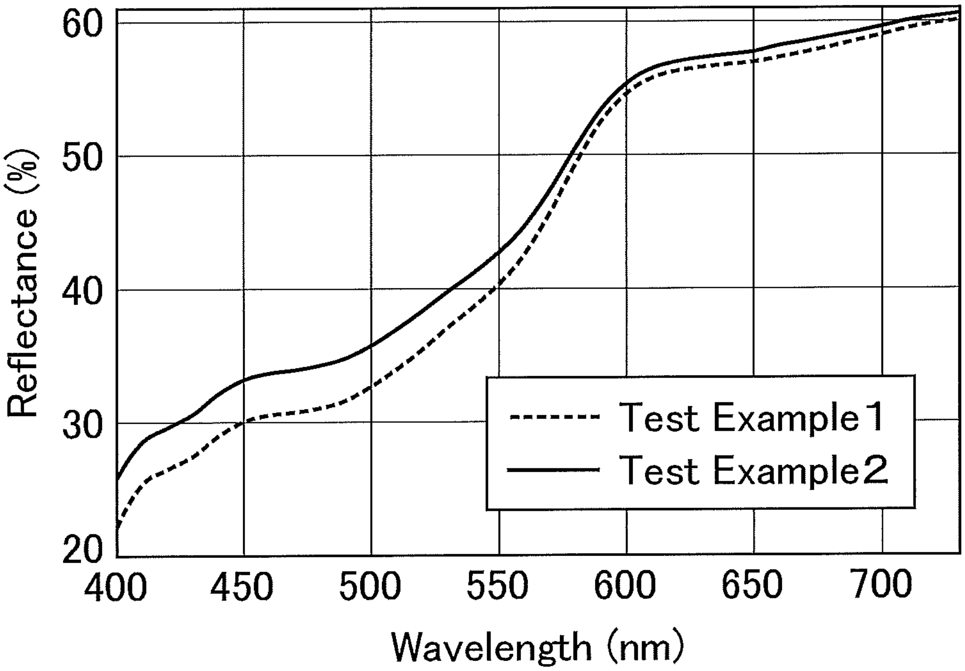
FIG. 8 shows the spectral reflectance measurement results of cosmetic application areas obtained in Test Example 1 (Comparative Example 7) and Test Example 2 (Example 11).

About 30 mg of the cosmetic product of Example 1 was applied to the area to which the base cosmetic product was applied in Test Example 1, such that a circle of the cosmetic product with a diameter of about 4 cm was formed (Test Example 2). Test Example 1 was taken as Comparative Example 7 and Test Example 2 was taken as Example 11. The spectral reflectance of the application area in each example was measured using CMS-35SPX (available from Murakami Color Research Laboratory Co., Ltd.). FIG. 8 shows the results.

The examples and comparative examples showed the following.

As shown in Table 1, the cosmetic products obtained in Examples 1 to 10 were evaluated to be excellent in the translucent sheen and the uniformity of the cosmetic film, and had a very good effect of enhancing the three-dimensional appearance under sunlight in the daytime on a sunny day. The excellent translucent sheen and excellent effect of enhancing the three-dimensional appearance were obvious also from the comparison with the phosphor-free cosmetic product of Comparative Example 1.

The cosmetic product obtained in Example 7 had a significantly high internal quantum efficiency as compared with the cosmetic product obtained in Example 1. This is because the cosmetic product obtained in Example 7 did not contain titanium oxide or iron oxide, and thus did not interfere with ultraviolet light or visible light required for excitation of the phosphors nor absorb the emission from the phosphors. The sensory evaluation further showed that it was possible to very clearly feel the effectiveness of the cosmetic product obtained in Example 7.

Meanwhile, the emission spectra of the cosmetic products obtained in Comparative Examples 2 to 6 emitted upon excitation by excitation light having a wavelength of 365 nm (FIGS. 4 and 5) had a fluorescence emission peak in only one of the range of 400 to 530 nm and the range of 620 to 720 nm. The cosmetic products obtained in Comparative Examples 2 to 6 showed significantly poor results in the translucent sheen, the uniformity of the cosmetic film, and the effect of enhancing the three-dimensional appearance as compared with the cosmetic products obtained in Examples 1 to 6.

FIG. 8 showed that applying the cosmetic product of Example 1 to the skin improves the reflectance in the blue to green range of 450 to 550 nm, thus making the skin look glowing brightly. It also improves the reflectance from 600 nm toward higher wavelengths, and thus gives translucency to the skin and makes the skin look beautiful while obstructing the appearance of blemishes, pores, and the like. This showed that the cosmetic product with a light reflection spectrum similar to the light reflection spectrum of a beautiful skin can makes the skin look beautiful and youthful.

The invention claimed is:

1. A cosmetic product comprising two or more phosphors each containing an inorganic compound, wherein the cosmetic product, upon excitation by excitation light having a wavelength of 365 nm, emits an emission spectrum having a fluorescence emission peak in each of the range of 400 to 530 nm and the range of 620 to 720 nm and having an $I_2/I_1$ of 1 to 30, where $I_1$ is a maximum emission intensity in the range of 530 to 620 nm and $I_2$ is a maximum peak intensity in the range of 620 to 720 nm, wherein the cosmetic product contains a mixture containing:

a phosphor containing at least one selected from the group consisting of a complex oxide containing Mn in a compound of the following formula (1), the Mn being present in a proportion of 0.00005 to 0.05 mol relative to 1 mol of magnesium in the compound:

$$Mg_xTi_yO_z \quad (1)$$

wherein x, y, and z satisfy $1.5<x<2.5$, $0.5<y\leq1.5$, and $z=x+2y$, and a complex oxide containing Mn in a compound of the following formula (2), the Mn being present in a proportion of 0.000042 to 0.0083 mol relative to 1 mol of aluminum in the compound:

$$Ca_xAl_yO_z \quad (2)$$

wherein x, y and z satisfy $0.1<x<1.05$, $11.9<y\leq12$, and $z=(2x+3y)/2$; and a phosphor containing at least one selected from the group consisting of a complex oxide containing Ce in a compound of the following formula (3), the Ce being present in a proportion of 0.0005 to 0.05 mol relative to 1 mol of phosphorus in the compound:

$$Ca_xP_yO_z \quad (3)$$

wherein x, y and z satisfy $3.2 \le x \le 5.0$, $1.9 \le y \le 2.1$, and $z = x+5$, and a fluorescent zinc oxide.

2. The cosmetic product according to claim 1, wherein the emission spectrum emitted upon excitation by excitation light having a wavelength of 365 nm has an $I_2/I_3$ of 1 to 40, where $I_3$ is a maximum peak intensity in the range of 400 to 530 nm and $I_2$ is the maximum peak intensity in the range of 620 to 720 nm.

3. The cosmetic product according to claim 1, wherein the cosmetic product has an emission color with an x value of the CIE chromaticity coordinates in the range of 0.25 to 0.55 and a y value of the CIE chromaticity coordinates in the range of 0.22 to 0.42 upon excitation by excitation light having a wavelength of 365 nm.

4. The cosmetic product according to claim 1, wherein the cosmetic product has a phosphor content of 0.1 to 20% by weight relative to the entire cosmetic product.

5. The cosmetic product according to claim 1, wherein the cosmetic product has an internal quantum efficiency of 1 to 40% upon excitation by excitation light having a wavelength of 365 nm.

6. The cosmetic product according to claim 1, which is in a form selected from powder foundations, liquid foundations, face powders, eye shadows, and makeup films.

7. The cosmetic product according to claim 1, wherein the emission spectrum emitted upon excitation by excitation light having a wavelength of 365 nm has a broad fluorescence peak in the range of 400 to 530 nm, and a distance between two points indicating half of a maximum peak intensity in the range of 400 to 530 nm is 50 to 200 nm.

* * * * *